US008145311B2

(12) United States Patent
Min

(10) Patent No.: US 8,145,311 B2
(45) Date of Patent: Mar. 27, 2012

(54) SYSTEMS AND METHODS FOR DETERMINING OPTIMAL ELECTRODE PAIRS FOR USE IN BIVENTRICULAR PACING USING MULTI-POLE VENTRICULAR LEADS

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 394 days.

(21) Appl. No.: 12/604,280

(22) Filed: Oct. 22, 2009

(65) Prior Publication Data
US 2011/0098772 A1  Apr. 28, 2011

(51) Int. Cl.
*A61N 1/00* (2006.01)
(52) U.S. Cl. .......................................... 607/28
(58) Field of Classification Search ...................... 607/28
See application file for complete search history.

(56) References Cited

U.S. PATENT DOCUMENTS

| 6,223,082 B1 * | 4/2001 | Bakels et al. ................... 607/17 |
| 7,248,925 B2 | 7/2007 | Bruhns et al. |

* cited by examiner

*Primary Examiner* — George Manuel

(57) ABSTRACT

Techniques are provided for use by implantable medical devices for determining a preferred or optimal pair of electrodes for delivering biventricular pacing therapy. In one example, the implantable device is equipped with a right ventricular (RV) lead and a multi-pole left ventricular (LV) lead. Briefly, for each of a selected set of RV/LV electrode pairs, electrocardiac parameters are detected within a patient in which the device is implanted, including parameters representative of an intrinsic biventricular electrical separation between LV and RV and parameters representative of a mechanical contraction delay in the LV. An optimal RV/LV electrode pair is then determined for delivering biventricular pacing based on an analysis of the intrinsic biventricular electrical separation and the mechanical contraction delay. Pacing latency, pacing delay from LV to RV, and the maximum slope of an LV evoked response may be used as proxies or surrogates for mechanical contraction delay.

19 Claims, 8 Drawing Sheets

FIG. 3

EXEMPLARY TECHNIQUE FOR DETERMINING OPTIMAL RV/LV ELECTRODE PAIR

STEP 1:

PERFORM SINGLE "V SENSE" (FIG. 4) TEST TO DETERMINE INTRINSIC ELECTRICAL SEPARATIONS ($\Delta_n$) BETWEEN THE RV TIP ELECTRODE AND EACH OF THE LV ELECTRODES ($LV_n$)

REJECT ANY RV/LV ELECTRODE PAIRS HAVING AN INTRINSIC ELECTRICAL SEPARATION LESS THAN 30 MS

— 200

STEP 2:

PERFORM A SET OF "LV PACE" TESTS (FIG. 5) USING INDIVIDUAL LV ELECTRODES TO DETERMINE A SURROGATE FOR MECHANICAL CONTRACTION DELAY SUCH AS LV PACING LATENCY (I.E. DELAY FROM PULSE TO PEAK OF LV EVOKED RESPONSE), AS WELL AS PACED INTERVENTRICULAR CONDUCTION DELAYS TO THE RV ($IVCD\_LR_n$), LV CAPTURE THRESHOLDS FOR EACH LV ELECTRODE, AND MAX EVOKED RESPONSE SLOPES ($D_{max}$)

REJECT ANY RV/LV ELECTRODE PAIRS WHERE THE LV ELECTRODE HAS A PACING LATENCY GREATER THAN 70 MS IF THE CAPTURE THRESHOLD ALSO EXCEEDS AN ACCEPTABLE LEVEL (E.G. 1.5xNORMAL) SO AS TO ELIMINATE UNSUITABLE ISCHEMIA/INFARCT SITES

— 222

STEP 3:

PERFORM A SINGLE "RV PACE" TEST (FIG. 6) TO DETERMINE PACING DELAYS FROM RV TO LV (I.E. $IVCD\_RL_n$) FOR EACH OF THE LV ELECTRODES

DETERMINE PREFERRED OR OPTIMAL $W_n$ PACING DELAYS FOR EACH RV/LV PAIR

DELIVER V PACING USING THE VARIOUS REMAINING RV/LV ELECTRODE PAIRS WHILE USING THE OPTIMAL $W_n$ PACING DELAYS

MEASURE WIDTHS OF EACH RESULTING PACED $LV_n$ QRS (SENSED VIA SURFACE/SUBQ ECG OR FAR-FIELD IEGM) AND ALSO MEASURE INTRINSIC LV QRS WIDTHS (I.E. NON-PACED $LV_n$ QRS)

— 242

SYSTEMS AND METHODS FOR DETERMINING OPTIMAL ELECTRODE PAIRS FOR USE IN BIVENTRICULAR PACING USING MULTI-POLE VENTRICULAR LEADS

FIELD OF THE INVENTION

The invention generally relates to implantable cardiac stimulation devices such as pacemakers and implantable cardioverter-defibrillators (ICDs) and, in particular, to technique determining pairs of electrodes for delivering biventricular pacing when using multi-pole ventricular leads.

BACKGROUND OF THE INVENTION

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may be performed at implantation and sometimes, a re-optimization may be performed during a follow-up consultation. While such optimizations are beneficial, the benefits may not last due to changes in various factors related to device and/or cardiac function.

The following patents and patent applications set forth various systems and methods for allowing a pacemaker, implantable cardioverter-defibrillator (ICD) or other cardiac rhythm management (CRM) device to determine and/or adjust AV/PV/VV pacing delays so as to help maintain the pacing delays at optimal values: U.S. patent application Ser. No. 10/703,070, filed Nov. 5, 2003, entitled "Methods for Ventricular Pacing"; U.S. patent application Ser. No. 10/974,123, filed Oct. 26, 2004; U.S. patent application Ser. No. 10/986,273, filed Nov. 10, 2004; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays" and U.S. patent application Ser. No. 12/132,563, filed Jun. 3, 2008, entitled "Systems and Methods for determining Intra-Atrial Conduction Delays using Multi-Pole Left Ventricular Pacing/Sensing Leads." See, also, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques are set forth within at least some of these patent documents for exploiting various inter-atrial and interventricular conduction delays to determine preferred or optimal AV/PV/VV pacing delays. Techniques are also set forth for exploiting the VV delays to determine which ventricles should be paced—the left ventricle (LV), the right ventricle (RV), both ventricles, or neither, and in which order. In at least some examples, the implanted device (or an external programming device in communication with the implanted device) performs a series of tests to determine intrinsic AV/PV and VV conduction delays from which preferred pacing delays are determined. In particular, an "A sense" test is performed to detect intrinsic intra-atrial delays from which preferred AV/PV pacing delays are determined. A "V sense" test is performed to detect intrinsic ventricular events from which an intrinsic interventricular conduction delay ($\Delta$) is determined. An "RV pace" test and a separate "LV pace" test are performed to detect paced interventricular conduction delays (IVCD_RL and IVCD_LR, respectively) from which an interventricular correction term ($\epsilon$) is determined. The optimal VV delay for use in biventricular pacing is then set based on $\Delta$ and $\epsilon$.

For implantable systems equipped with multi-pole LV leads (i.e. leads with a set of LV electrodes for pacing/sensing at different sites on or within the LV), special techniques may be employed to perform the various tests to determine values for $\Delta$ and $\epsilon$ for use in determining the VV delays for use with the various LV electrodes. In particular, see U.S. patent application Ser. No. 12/507,646, of Min, filed Jul. 22, 2009, entitled "Systems and Methods for Optimizing Ventricular Pacing Delays for use with Multi-Pole Leads" which sets forth improved techniques for determining VV delays for use with multi-pole LV leads. See, also, U.S. patent application Ser. No. 12/507,679, of Min, filed Jul. 22, 2009, entitled "Systems and Methods for Optimizing Ventricular Pacing Delays during Atrial Fibrillation", which describes special techniques for performing V sense, RV pace and LV pace tests during atrial fibrillation (AF.) These last two documents are incorporated by reference herein in their entirety.

When employing a multi-pole LV lead, it is also useful to identify an optimal pair of LV/RV electrodes for use in delivering biventricular pacing (i.e. to identify an optimal pacing site) and it is to this end that aspects of the invention are directed.

SUMMARY OF THE INVENTION

In an exemplary embodiment, a method is provided for use by an implantable cardiac rhythm management device equipped with an RV lead (having at least one RV electrode) and a multi-pole LV lead (having a plurality of LV electrodes.) Briefly, for each of a selected set of RV/LV electrode pairs, electrocardiac parameters are detected within a patient in which the device is implanted, including parameters representative of an intrinsic biventricular electrical separation between LV and RV and parameters representative of a mechanical contraction delay in the LV. An RV/LV electrode pair is then determined for delivering biventricular pacing based on the intrinsic biventricular electrical separation and the mechanical contraction delay.

In an illustrative embodiment, a series of broad steps or procedures are performed to collect various electrocardiac parameters and to determine an optimal RV/LV electrode pair from the parameters.

During a first broad step, a V sense test is performed to detect, for each of the RV/LV electrode pairs, an amount of intrinsic electrical separation ($\Delta_n$) between the RV electrode and the LV electrode ($LV_n$) of the pair. Any RV/LV electrode pair that has an intrinsic electrical separation of less than 30 milliseconds (ms) is rejected for the purposes of biventricular pacing. Preferably, only a single V sense test is performed to determine the $\Delta_n$ values for all of the RV/$LV_n$ electrode pairs.

During a second broad step, a set of LV pace tests are performed to detect, for each of the LV electrodes of the remaining RV/LV pairs, a pacing latency ($PL_n$) value based on LV pacing pulses delivered using the LV electrode. That is, for each LV electrode ($LV_n$), an LV pulse ($LV_n$-pulse) is delivered and then the evoked response ($ER_n$) is detected at the $LV_n$ electrode. The time delay from the LV pulse to the peak of $ER_n$ is the pacing latency $PL_n$ for that particular LV electrode. In one particular example, a series of LV pace tests are performed by delivering LV(i)-pulses to each of the LVn electrodes and then sensing resulting QRS at the rest of LV electrodes and RV QRS complexes at the RV electrode.

During the LV pace test, additional data is preferably also collected, including capture thresholds for each of the LV electrodes, pacing delays from each of the LV electrodes to the RV (IVCD_$L_n$R), and the maximum slope values of LV ER (Dmax$_n$.) Sites with long pacing latency might be within ischemia/infarct zones. Pacing within these zones is appropriate so long as the capture threshold for the site is not too high. Accordingly, in one example, RV/LV electrode pairs are rejected for the purposes of biventricular pacing if the pacing latency for the LV electrode of the pair is greater than 70 ms and the capture threshold at the LV electrode is more than 1.5 times normal.

During a third broad step, an RV pace test is performed to detect, for each of the remaining RV/LV electrode pairs, the pacing delay from the RV electrode to the LV (i.e. IVCD_$RL_n$.) The device then uses the IVCD_$RL_n$ values along with the IVCD_$L_n$R values to determine interventricular correction terms ($\epsilon_n$). Preferred VV pacing delays are then determined for each of the RV/LV pairs using the $\Delta_n$ values and the $\Delta_n$ values:

$$VV_n = \alpha_n(\Delta_n + \epsilon_n)$$

where $\alpha_n$ is 0.5 (or other suitable coefficient) and where $$\epsilon_n = IVCD\_L_nR - IVCD\_RL_n.$$

Biventricular pacing is delivered using the $VV_n$ pacing delay values and paced LV QRS complexes are detected at each LV electrode. Morphological parameters, particularly paced LV QRS width, are measured for each of the paced LV QRS complexes. Intrinsic LV QRS width is also preferable determined. Paced and intrinsic LV QRS width can be determined, for example, based on far-field IEGM signals or from ECG signals (if available.)

During a fourth broad step, the device determines the optimal RV/LV electrode pair (from among the remaining pairs that have not yet been rejected) based on the data collected in the various tests. In one example, the RV/LV electrode pair having the shortest paced LV QRS width is selected for use in delivering biventricular pacing so long as the paced LV QRS width is less than the corresponding intrinsic LV QRS width. In another example, the RV/LV electrode pair having a mechanical contraction delay in a preferred range is selected for use in delivering biventricular pacing, wherein pacing latency, pacing delay, and Dmax are used as proxies or surrogates for mechanical contraction delay. That is, the RV/LV electrode pair having the appropriate LV pacing latency, the appropriate pacing delay from RV to LV, or the appropriate LV Dmax is selected for use in delivering biventricular pacing. In some patients, the longest contraction delay might be the preferred or appropriate delay.

Although described primarily with respect to implementations having a multi-pole LV lead, aspects of the invention are also applicable to multi-pole RV leads and to multi-pole atrial leads as well. More generally, a method is provided for use by an implantable cardiac rhythm management device equipped with a plurality of cardiac pacing/sensing electrodes wherein, for each of a selected set of electrode pairs, electrocardiac parameters are detected within a patient in which the device is implanted including parameters representative of an intrinsic electrical separation between a pair of cardiac chambers and parameters representative of a mechanical contraction delay in one of the chambers, and wherein an electrode pair is determined for delivering bipolar pacing based on the intrinsic electrical separation and the mechanical contraction delay.

System and method implementations of various exemplary techniques are presented herein.

BRIEF DESCRIPTION OF THE DRAWINGS

Features and advantages of the described implementations can be more readily understood by reference to the following description taken in conjunction with the accompanying drawings.

FIG. 3 is a flowchart illustrating an exemplary biventricular implementation of the technique of FIG. 2 wherein a set of four broad steps are performed to determine the optimal pair of RV/LV electrodes;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
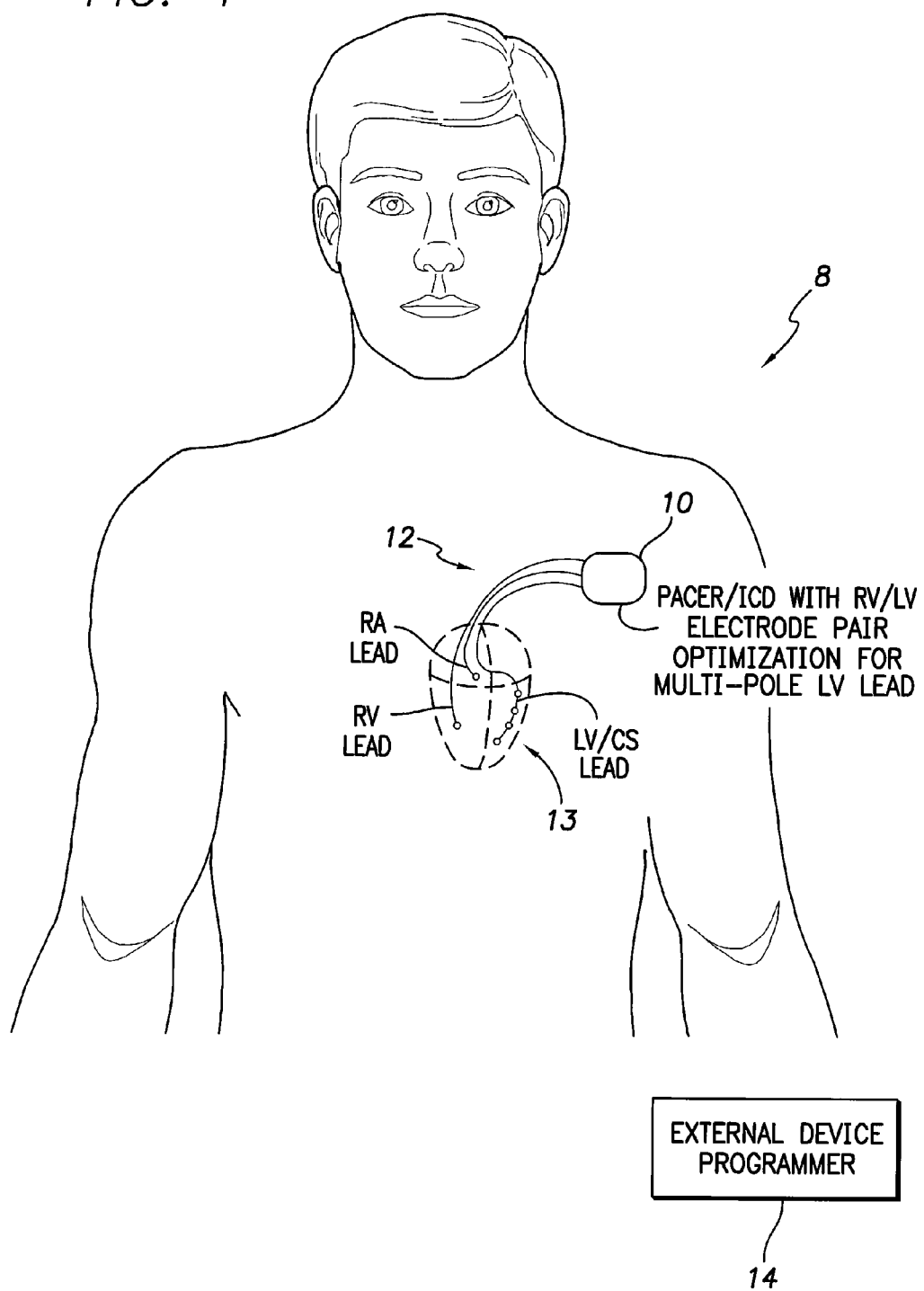
FIG. 1 illustrates pertinent components of an implantable medical system having a pacemaker or ICD equipped to determine an optimal pair of RV/LV electrodes for biventricular pacing for use with multi-pole ventricular leads.

FIG. 1 illustrates an implantable medical system 8 capable of determining preferred or optimal RV/LV electrode pairs. The medical system 8 includes a pacer/ICD 10 or other cardiac rhythm management device equipped with one or more cardiac sensing/pacing leads 12 implanted on or within the heart of the patient, including a multi-pole LV lead implanted via the coronary sinus (CS). In FIG. 1, a stylized representation of the set of leads is provided. To illustrate the multi-pole configuration of the LV lead, a set of electrodes 13 is shown distributed along the LV lead. The RV and RA leads are each shown with a single electrode, though each of those leads may include additional electrodes as well, such as tip/ring electrode pairs, or shocking coils. Still further, the LV lead can also include one or more left atrial (LA) electrodes mounted on or in the LA via the CS. See FIG. 7 for a more complete and accurate illustration of various exemplary leads.

In some implementations, the pacer/ICD itself determines the optimal RV/LV electrode pair based on electrocardiac signals sensed using the leads. In other implementations, the device transmits parameters derived from electrocardiac signals sensed within the patient to an external device programmer 14 that performs the optimization. That is, the device programmer determines the optimal RV/LV electrode pair (typically under the supervision of a clinician), which is then programmed into the pacer/ICD via telemetry. Other external devices might instead be used to perform the optimization, such as bedside monitors or the like. In some embodiments, the device programmer or bedside monitor is directly networked with a centralized computing system, such as the HouseCall™ system or the Merlin@home/Merlin.Net systems of St. Jude Medical.

In the following examples, it is assumed that the pacer/ICD determines the optimal RV/LV pair using on-board components. An example where the external programmer performs the optimization is discussed below with reference to FIG. 8.

LV/RV Electrode Pair Optimization

Figure 2:
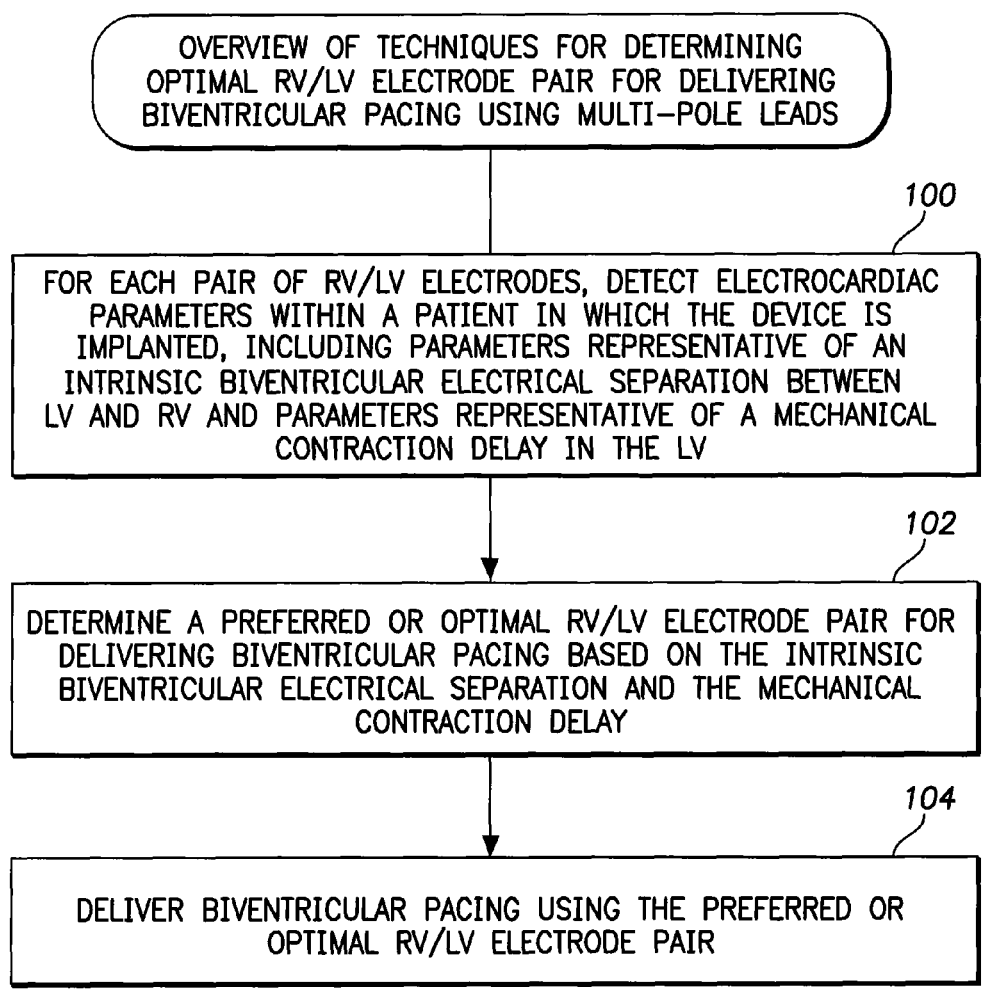
FIG. 2 is a flowchart providing an overview of a technique for determining an optimal pair of RV/LV electrodes for biventricular pacing, which may be performed by the system of FIG. 1.

FIG. 2 broadly summarizes a general technique for determining preferred or optimal RV/LV electrode pairs for use with a multi-pole ventricular lead that may be exploited by the pacer/ICD of FIG. 1 or other suitably equipped systems. Beginning at step 100, for each pair of RV/LV electrodes that can be selected for biventricular pacing from among the electrodes of the LV and RV leads, the pacer/ICD detects electrocardiac parameters within the patient, including parameters representative of an intrinsic biventricular electrical separation between LV and RV and parameters representative of a mechanical contraction delay in the LV (including, e.g., pacing latency in the LV.) In the example of FIG. 1, where the LV lead has four pacing/sensing electrodes for use in delivering biventricular pacing in combination with a single RV (tip) electrode, there are four RV/LV electrode pairs that can be selected for biventricular pacing: $LV_1/RV$, $LV_2/RV$, $LV_3/RV$, $LV_4/RV$. The aforementioned parameters are determined for each of the four RV/LV electrode pairs.

At step 102, the pacer/ICD determines a preferred or optimal RV/LV electrode pair for delivering biventricular pacing based on (at least) the intrinsic biventricular electrical separation and the mechanical contraction delay. In this regard, as will be explained, a series of tests may be performed to collect various parameters for each of the candidate pairs of electrodes. Some of the electrode pairs might be rejected for one reason or another, such as if a particular electrode pair lacks sufficient electrical separation. A preferred or optimal pair is then selected from among the pairs that have not been rejected, with the selection made based on an analysis of the various electrical separation and the mechanical contraction delay parameters determined for those pairs.

At step 104, the pacer/ICD then delivers biventricular pacing using the preferred or optimal RV/LV electrode pair determined at step 102. The actual delivery of biventricular pacing may proceed in accordance with otherwise conventional biventricular pacing techniques, such as CRT techniques.

In the examples described herein, the multi-pole ventricular lead is an LV lead, but it should be understood that aspects of the invention are applicable to multi-pole RV leads. Indeed, the techniques are applicable to implementations wherein both the LV and RV have multi-pole leads. Still further, the techniques are also generally applicable to multi-pole atrial leads, implanted on or in either the RA or the LA. As such, at least some of the techniques described herein are generally applicable to optimizing various "interchamber" pacing delays.

Thus, FIG. 2 summarizes a broad technique for determining an optimal RV/LV pair for biventricular pacing. It should be understood that the optimal pair is not necessarily truly optimal in any particular quantifiable sense. As can be appreciated, what constitutes a truly "optimal" electrode pair depends on the criteria used for judging the resulting pacing performance, which can be subjective in the minds of some clinicians. The RV/LV electrode pair determined using the method of FIG. 2 represents, at least, a "preferred" RV/LV pair. Clinicians may choose to adjust or alter the selection via device programming for particular patients, at their discretion.

FIGS. 3-6 provide a more detailed example wherein an optimal RV/LV electrode pair is determined for biventricular pacing between an RV tip electrode and a multi-pole LV lead having N electrodes (individually denoted LVn).

Beginning at step 200, the pacer/ICD performs a first broad step wherein a "V sense" test is performed to determine intrinsic electrical separations ($\Delta_n$) between the RV tip electrode and each of the LV electrodes ($LV_n$). Any RV/LV electrode pairs having an intrinsic electrical separation less than a predetermined minimum acceptable threshold (such as 30 ms) are rejected for the purposes of biventricular pacing.

During the V sense test, the pacer/ICD: detects P-waves on an A-IEGM channel sensed using an RA lead and/or delivers A-pulse to the RA using the RA lead. The P-waves may be detected during a contemporaneous A sense test. The A-pulses may be delivered during a contemporaneous A pulse test. That is, the V sense test may be performed at the same time as A sense/A pace tests to enhance overall test efficiency. See the patent documents cited above for discussions of A sense/A pace tests, which are generally used to determine intra-atrial (AE/PE) delays for use in setting atrioventricular pacing delays (AV/PV).

Also at step 200, during the V sense test, the pacer/ICD senses RV-IEGM and N individual LVn-IEGM signals along N sensing vectors between the RV tip electrode and each of the respective LVn electrodes. The device also detects LVn-QRS events within the LVn-IEGMs and detects RV-QRS events within the RV-IEGM. Exemplary RV and LVn IEGMs are shown in FIG. 4 (in stylized form) for a quadra-pole example wherein the LV lead has four pacing/sensing electrodes.

Figure 4:
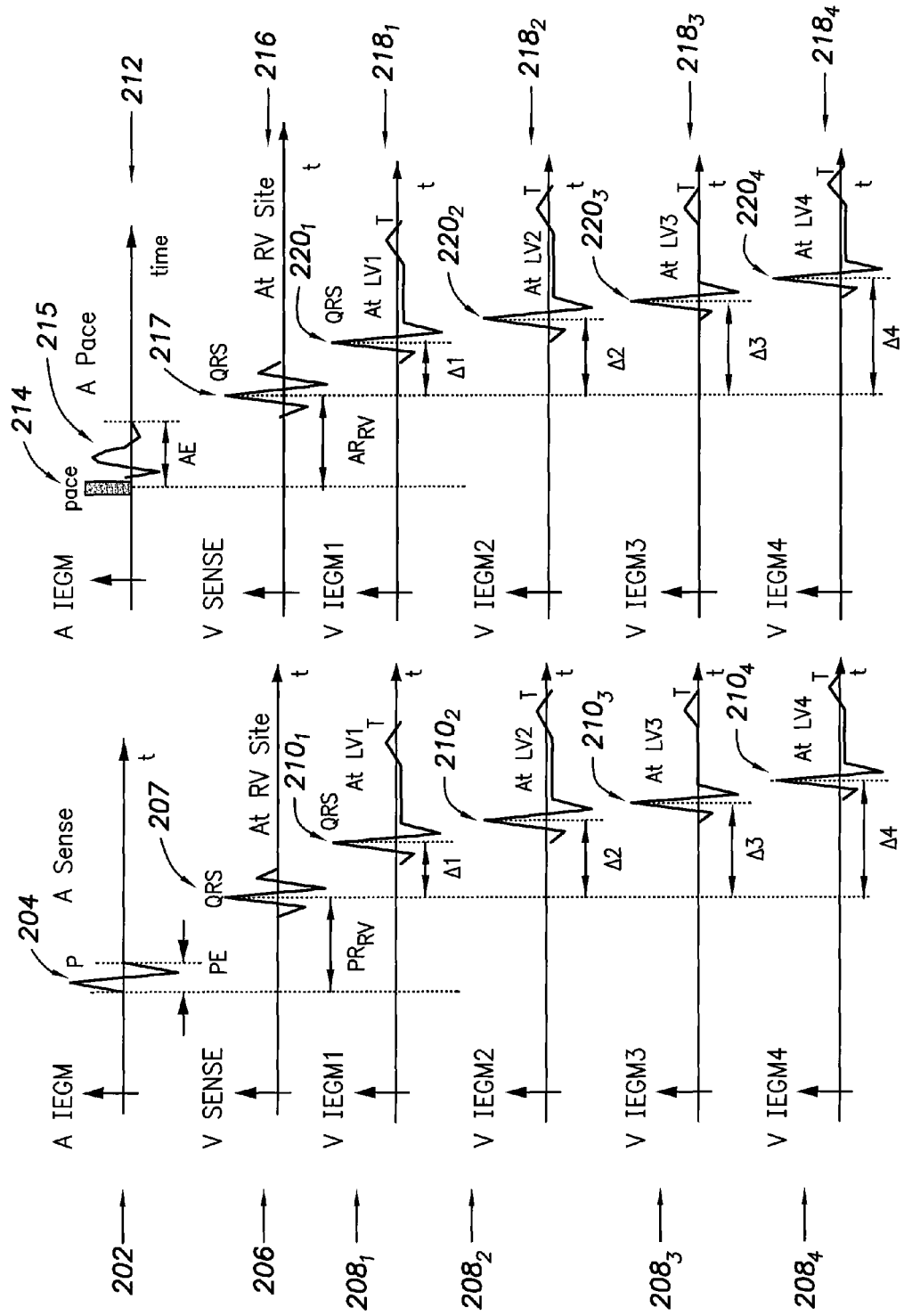
FIG. 4 is a graph illustrating an exemplary A-IEGM, RV-IEGM and set of LVn-IEGMs during a V sense test exploited during a first broad step of the technique of FIG. 3.

More specifically, FIG. 4 illustrates, on its left-hand side, an A-IEGM 202 containing a P-wave 204. An RV IEGM 206 includes an RV QRS complex 207 triggered by the P-wave via AV conduction. A set of four LV IEGMs $208_1$-$208_4$ are shown. Each includes a version of a single LV QRS triggered by the P-wave via AV conduction, but sensed at slightly different times. The different versions of the LV QRS complex triggered by the P-wave are denoted $210_1$-$210_4$. FIG. 4 also illustrates, on its right-hand side, an A-IEGM 212 containing an A-pulse 214 and resulting atrial evoked response (ER) 215. (The ER may be detected to verify capture of the atrial pulse and, if necessary, the atrial pulse magnitude can be increased to compensate for any persistent lack of capture.)

An RV IEGM 216 includes an RV QRS complex 217 triggered by the A-pulse via AV conduction. A set of four LV IEGMs $218_1$-$218_4$ are shown. Each includes a version of a single LV QRS triggered by the A-pulse via AV conduction, but sensed at slightly different times, denoted $220_1$-$220_4$. In FIG. 4, the T-wave associated with each QRS is identified by the letter "T".

As part of the V sense test, the device measures or otherwise determines $\Delta_n$ between the RV QRS and each of the N LVn QRS complexes on the N LVn IEGM channels. As noted, the $\Delta_n$ values represent the intrinsic electrical separation between RV and LV. That is, $\Delta_1$ represents the intrinsic electrical separation for electrode pair RV/LV$_1$; $\Delta_2$ represents the intrinsic electrical separation for electrode pair RV/LV$_2$; and so on. Each of these values is compared against the minimum acceptable threshold (of, e.g., 30 ms) and any electrode pairs have $\Delta$ values below the threshold are rejected for the purposes of biventricular pacing. Note that the $\Delta$ values can be negative. If negative, the LV depolarizes first then the RV. If positive, the RV depolarizes first, then the LV. Accordingly, it is the absolute value (or magnitude) of the $\Delta$ values that is compared against the threshold. Also, due to beat-to-beat variation, preferably a sufficient number of $\Delta$ values are detected and measured for each RV/LV pair to permit the device to calculate suitable average values of $\Delta$ for comparison against the threshold. For example, a series intervals may be detected and recorded over a predetermined period of time (such as over one minute) or for a predetermined number of heartbeats (such as at least eight beats) to permit suitable average values for each of $\Delta_n$ to be determined.

Particularly efficient techniques for performing V sense tests with multi-pole electrodes are discussed in U.S. patent application Ser. No. 12/507,646, filed Jul. 22, 2009, cited above.

Returning to FIG. 3, at step 222, the pacer/ICD the performs a second broad step wherein a set of "LV PACE" tests are performed using individual LV electrodes to determine LV pacing latency values (i.e. the delay from LV pulse to the peak of the LV evoked response), as well as paced interventricular conduction delays to the RV (IVCD_L$_n$R), LV capture thresholds for each LV electrode, and max evoked response slopes (Dmax), again for each of the n LV electrodes. It should be noted that the LV pacing latency values and the max evoked response slopes (Dmax) determined during step 222 can serve as surrogates or proxies for mechanical delay (which is exploited later during the selection of a particular RV/LV electrode pair in step 280.) If the pacer/ICD is equipped to directly detect mechanical contraction delays, then surrogates need not be used.

Once the information has been acquired, the pacer/ICD rejects any RV/LV electrode pairs where the LV electrode has a pacing latency greater than 70 ms if the capture threshold also exceeds an acceptable level (e.g. 1.5 times normal) so as to eliminate unsuitable ischemia/infarct sites. As already noted, pacing within these zones is appropriate so long as the capture threshold for the site is not too high. Accordingly, in the example of FIG. 3, RV/LV electrode pairs are rejected for the purposes of biventricular pacing if the pacing latency for the LV electrode of the pair is greater than 70 ms and the capture threshold at the LV electrode is more than 1.5 times normal. (Additionally or alternatively, if pacing latency or pacing delay is abnormally longer than a pre-determined threshold, such as if the pacing delay (pacing pulse to the peak of QRS) is longer than 70 ms, a correction term may be added to AV/PV delay as described in the application cited above. For example, see application Ser. Nos. 12/328,605 and 12/132,563.)

Insofar as the LV pace tests are concerned, a set of N LV pace tests is performed, one test for each of the N LV electrodes. Briefly, the pacer/ICD delivers an LV pacing pulse using a selected one of the N LV electrodes of the LV lead. For example, an LV pulse may be delivered in a unipolar configuration between a selected LV electrode (such as "distal" or "tip" electrode LV$_1$) and the device housing. Alternatively, the pulse may be delivered in a bipolar configuration between any two adjacent LV electrodes, such as between LV$_1$ and LV$_2$, or between LV$_2$ and LV$_3$, or between LV$_3$ and LV$_4$ (i.e. the proximal LV lead.) These are just some examples. In general, bipolar pulses may be delivered LVn to LV(n−1) or LV(n+1). Still further, other combinations of LV electrodes can potentially be used to deliver pulses in the bipolar pulse configuration, such as LV$_1$ to LV$_4$, though adjacent electrode pairs are preferred. In any case, pacer/ICD then detects a resulting RV QRS complex on the RV channels and measures the time delay between the LV pulse and the RV QRS complex (or RV paced propagation) detected on the RV IEGM channel. The device also sets IVCD_L$_n$R based on the time delay from the LV pulse to RV QRS complex. The device then selects another of the LVn electrodes and repeats this process until a value for IVCD_LR has been determined for each of the N electrodes of the multi-pole LV lead.

In one particular example, a series of LV pace tests are performed by delivering LV(i)-pulses to each of the LVn electrodes and then sensing resulting QRS at the rest of LV electrodes and RV QRS complexes at the RV electrode. IVCD_L(j)L(i) and IVCD_L(1)R values are separately measured based on the timing of the LV(j)-pulses and the timing respective QRS at the rest of LV electrodes and RV QRS complexes.

Figure 5:
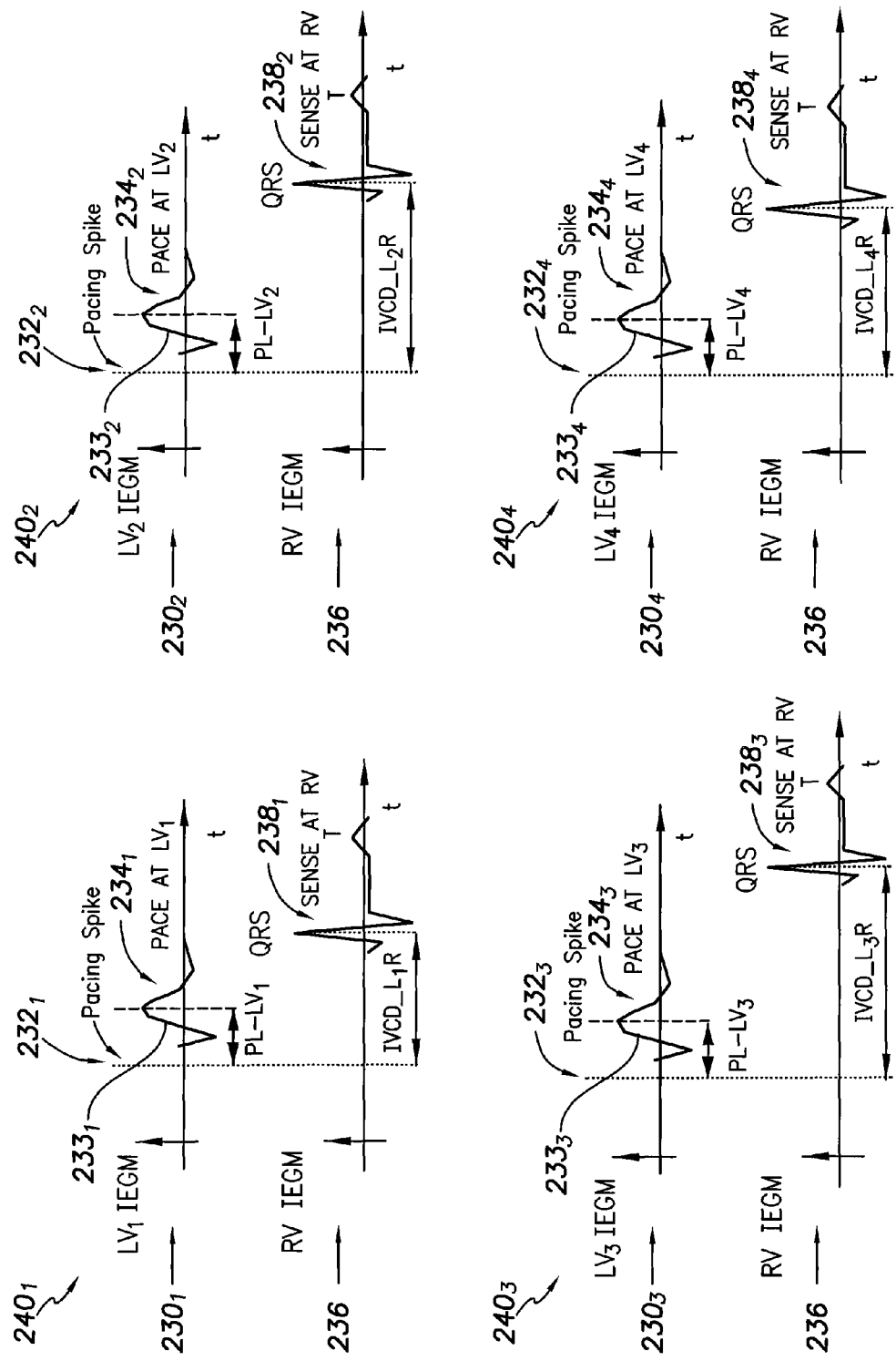
FIG. 5 includes several graphs illustrating various RV IEGMs and LVn IEGMs sensed during a set of LV pace tests exploited during a second broad step of the technique of FIG. 3.

Exemplary RV and LVn IEGMs are shown in FIG. 5 for a quadra-pole example of the LV pace test. More specifically, FIG. 5 illustrates a first LV pace test 240$_1$ wherein an LV pulse 232$_1$ is delivered via electrode LV$_1$, triggering an LV evoked response 234$_1$ (which may be used to verify capture.) The LV evoked response is shown on an LV$_1$ IEGM sensed using the LV$_1$ electrode. The delay (PL-LV$_n$) between the LV pulse and the LV evoked response is the pacing latency for that particular LV electrode. The pacer/ICD also determines for the first LV electrode, the capture threshold for the LV electrode, i.e. the minimum pulse energy or needed to trigger an evoked response within the LV. Otherwise conventional techniques may be employed to determine the capture threshold. Still further, the pacer/ICD determines the maximum slope 233 of the evoked response for LV$_1$, which it stores as Dmax$_1$. Again, otherwise conventional techniques may be employed to determine Dmax.

The LV pulse also triggers an RV QRS (or RV paced propagation) 238$_1$ via interventricular conduction, which is shown on an RV IEGM 236. The IVCD_LR interval between the LV pulse and the RV QRS is shown as IVCD_L$_1$R. This interval is the paced interventricular conduction delay from LV to RV, which is used, as described below, to determine an interventricular correction term for use in setting a preferred interventricular pacing delay.

Preferably, a sufficient number of LV-pulses are delivered to permit the device to calculate average values for the various parameters (PL_LV$_1$, IVCD_L$_1$R, Dmax$_1$, and capture threshold LV$_1$).

Similar tests are performed for the other LV electrodes. Briefly, a second LV pace test 240$_2$ is shown wherein an LV pulse 232$_2$ is delivered via electrode LV$_2$, triggering an LV evoked response 234$_2$. The LV evoked response is shown on an LV$_2$ IEGM sensed using the LV$_2$ electrode along with the corresponding pacing latency value PL-LV$_2$. Dmax and the capture threshold for LV$_2$ are also determined. The LV pulse also triggers an RV QRS 238$_2$ (which is shown on RV IEGM 236) and the IVCD interval IVCD_LR$_2$ is measured. A third LV pace test 240$_3$ is shown wherein an LV pulse 232$_3$ is delivered via electrode LV$_3$, triggering an LV evoked response 234$_3$. The LV evoked response is shown on an LV$_3$ IEGM sensed using the LV$_3$ electrode. The LV pulse also triggers an RV QRS $238_3$ (which is shown on RV IEGM 236) and the IVCD interval IVCD_$LR_3$ is measured. A fourth LV pace test $240_4$ is shown wherein an LV pulse $232_4$ is delivered via electrode $LV_4$, triggering an LV evoked response $234_4$. The LV evoked response is shown on an $LV_4$ IEGM sensed using the $LV_4$ electrode. The LV pulse also triggers an RV QRS $238_4$ (which is shown on RV IEGM 236) and the IVCD interval IVCD_$LR_4$ is measured.

The various RV QRS events occur at slightly different times relative to the respective LV pulses and hence the values for IVCD_LR are all slightly different. Likewise, values for pacing latency, capture threshold and Dmax may also differ for each LV electrode. In any case, the various values are recorded for use in step 222 of FIG. 3 to reject LV/RV electrode pairs (if warranted) based on pacing latency in view of capture threshold.

Returning again to FIG. 3, at step 242, the pacer/ICD the performs a second broad step wherein a single "RV PACE" test is performed to determine pacing delays from RV to LV (I.E. IVCD_$RL_n$) for each of the remaining LV/RV electrode pairs. It should be noted that the pacing delays from RV to LV can also serve as a surrogate or proxy for mechanical delay (which is exploited later in the actual selection of a particular RV/LV electrode pair in step 280.)

At step 242, the device also determines optimal $VV_n$ pacing delays for each remaining RV/LV pair. This may be performed, e.g., using techniques described in application Ser. No. 12/507,646, filed Jul. 22, 2009, cited above. Briefly, in one example, the device detects, for each of the remaining RV/LV electrode pairs, the pacing delay from the RV electrode to the LV (i.e. IVCD_RL(n).) The device then uses the IVCD_RL(n) values along with the IVCD_L(n)R values to determine interventricular correction terms ($\epsilon_n$). Preferred VV pacing delays are then determined for each of the RV/LV pairs using the $E_n$ values and the $\Delta_n$ values:

$$VV_n = \alpha_n(\Delta_n + \epsilon_n)$$

where $\alpha_n$ is 0.5 (or other suitable coefficient) and where $$\epsilon_n = IVCD\_L_nR - IVCD\_RL_n.$$

As to the coefficient $\alpha_n$, $\alpha_n$ is a programmable or hard-coded parameter that may vary from patient to patient and from electrode to electrode. In some examples, each of the $\alpha_n$ values is set to 0.5, which is a default value. Otherwise routine testing may be employed to determine preferred or optimal values for $\alpha_n$ based, e.g., on an evaluation of the resulting hemodynamics within test patients. The values for $\alpha$ values may differ from electrode to electrode, i.e. $\alpha_1$ may be set to a different value than $\alpha_2$.

It should be understood that these VV values are not necessarily truly optimal in any particular quantifiable sense. As can be appreciated, what constitutes a truly "optimal" value depends on the criteria used for judging the resulting performance, which can be subjective in the minds of some clinicians. The VV value determined using the method of FIG. 3 represents, at least, a "preferred" VV value. Clinicians may choose to adjust or alter the value via device programming for particular patients, at their discretion.

Once the preferred or optimal $VV_n$ pacing delays have been determined, the device then delivers VV pacing using the various remaining RV/LV electrode pairs (and while using the optimal $VV_n$ pacing delays) and measures the widths of each resulting paced $LV_n$ QRS (sensed via a surface/subQ ECG or via a far-field IEGM.) The pacer/ICD also measures intrinsic LV QRS widths (i.e. non-paced $LV_n$ QRS) during periods of time when VV pacing is not performed.

To perform the RV pace test of step 242, the pacer/ICD delivers an RV pacing pulse using the RV lead (which may include a tip/ring electrode pair for delivery of bipolar pulses to the RV) and then detects resulting LVn QRS complexes on each of the N LVn channels. The device measures time delays between the RV pulse and each of the LV QRS complexes detected on the N LVn IEGM channels and, for each n, the device sets IVCD_RLn based on the time delays from the RV pulse to LVn QRS.

Particularly efficient techniques for performing RV pace tests with multi-pole electrodes are discussed in U.S. patent application Ser. No. 12/507,646, filed Jul. 22, 2009, cited above.

Note that paced LV QRS width can be measured either from surface ECG (min to max from multiple vectors such as 12 lead ECG) or IEGMs of atrial ventricular far-field or non-paced V sites. When using far-field IEGMs, the far-field IEGMs can be sensed along a plurality of sensing vectors with the paced QRS width then determined based on the time from the beginning of a first QRS event detected within the sensing vectors to the end of a last QRS event detected within the sensing vectors. If a surface ECG is to be used, the paced QRS width data may be initially collected by a clinician using the surface ECG, then programmed into the device. If the implanted system includes sub-Q leads, it may also be possible to determine the LV QRS width using the sub-Q leads.

Figure 6:
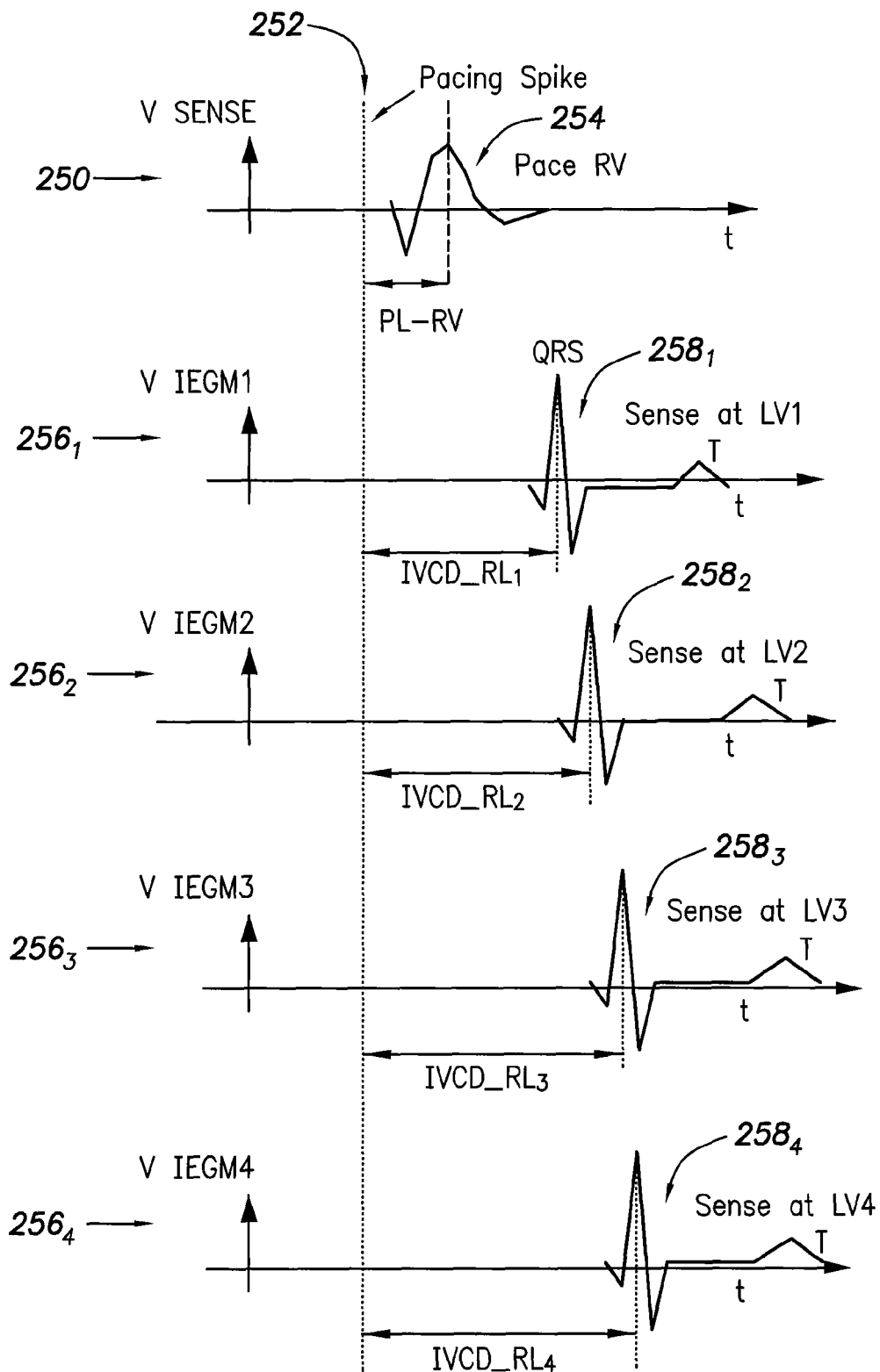
FIG. 6 is a graph illustrating an exemplary RV-IEGM and set of LVn-IEGMs during an RV pace test exploited during a third broad step of the technique of FIG. 3.

Exemplary RV and LVn IEGMs are shown in FIG. 6 (in stylized form) for a quadra-pole example of the RV pace test. More specifically, FIG. 6 illustrates an RV IEGM 250 that includes an RV evoked response 254 triggered by an RV-pulse 252. (The ER may be detected to verify capture of the RV pulse and, if necessary, the RV pulse magnitude can be increased to compensate for any persistent lack of capture.) A set of four LV IEGMs $256_1$-$256_4$ are shown. Each includes a version of a single LV QRS (or an LV "paced propagation") triggered by the RV-pulse via interventricular conduction, but sensed at slightly different times. The LV QRS complexes triggered by the RV-pulse are denoted $258_1$-$258_4$. The IVCD_RLn intervals are also shown.

Thus, a single RV-pulse can be used to ascertain values for IVCD_RLn without needing to perform a separate RV pace test for each separate LVn electrode, thus saving time. Preferably a sufficient number of RV-pulses and resulting IVCD_RLn intervals are detected and measured to permit the device to calculate suitable averages.

Returning to FIG. 3, at step 280, the pacer/ICD then selects the optimal LV/RV pair from the remaining pairs using one of two exemplary techniques:

(1) the pacer/ICD selects the RV/LV electrode pair having shortest paced LV QRS width so long as the paced LV QRS width for the pair is less than the intrinsic LV QRS width for the same pair; or (2) the pacer/ICD selects the RV/LV electrode pair having an appropriate or preferred range of mechanical latency, which, in some patients, might be the longest surrogate for mechanical contraction delay (i.e. longest LV pacing latency, longest pacing delay from RV to LV or largest Dmax value.)

The choice depends on the pre-programming of the pacer/ICD as may be specified, e.g., by a clinician during a programming session using a device programmer.

Considering these choices in more detail, in the first example, the pacer/ICD compares, for each remaining RV/LV electrode pair, the paced LV QRS width (determined within step 242) against the non-paced LV QRS width (also determined within step 242). The pacer/ICD rejects any RV/LV pairs where the paced LV QRS width is not less than the non-paced LV QRS width. The pacer/ICD then selects the RV/LV pair having the shortest paced LV QRS width from among the remaining LV/RV pairs that have not yet been rejected.

In the second example, the pacer/ICD examines, for each remaining RV/LV electrode pair, the various values already determined that serve as surrogates for mechanical pacing delay, particularly LV pacing latency, and the Dmax value (which were determined during step 222) and the pacing delay from RV to LV (which was determined during step 242.) The pacer/ICD then selects the RV/LV pair having the longest surrogate for mechanical delay. In one example, the pacer/ICD may be preprogrammed to use only one of these surrogate values, such as LV pacing latency, to select the RV/LV pair. In other examples, the pacer/ICD may be programmed to use some combination of surrogate values, such as by calculating a combined metric value based on the various surrogates.

Note that, in the event that all RV/LV pairs have been rejected for one reason or another, appropriate warning/notification signals can be provided to the clinician. A default RV/LV pair (such as the RVtip/LVtip pair) can be used to deliver any needed VV pacing pending review by a clinician.

At step 282, the pacer/ICD then delivers biventricular pacing to the patient using the selected RV/LV electrode pair and with the optimal VV pacing delays. Where appropriate, the biventricular pacing can be delivered in conjunction with other pacing therapy techniques, such as other CRT techniques. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias.

The procedure of FIG. 3 can be repeated periodically or on demand to update the selection of the RV/LV electrode pair. Also note that, in some examples, the pacer/ICD might be programmed to deliver VV pacing using a multiple pairs of electrodes rather than only a single RV/LV electrode pair. For example, the two "best" electrode pairs could be selected for providing VV pacing along two vectors. As can be appreciated, a variety of modifications can be provided to the techniques or FIG. 3, which merely serves as an example.

Although primarily described with respect to examples having a pacer/ICD, other implantable medical devices may be equipped to exploit the techniques described herein such as CRT devices and CRT-D devices. For the sake of completeness, an exemplary pacer/ICD will now be described, which includes components for performing the functions and steps already described.

Furthermore, although examples described herein involve processing of data by the implanted device itself to select the optimal electrode pair, some operations might be performed using an external device, such as a bedside monitor, device programmer, computer server or other external system. For example, data collected by the pacer/ICD can be transmitted to an external device, which then processes the data select the optimal electrode pair, which is then programmed into the pacer/ICD. Processing by the implanted device itself is preferred as that allows the device to repeat the selection process periodically or as needed.

Exemplary Pacer/ICD

Figure 7:
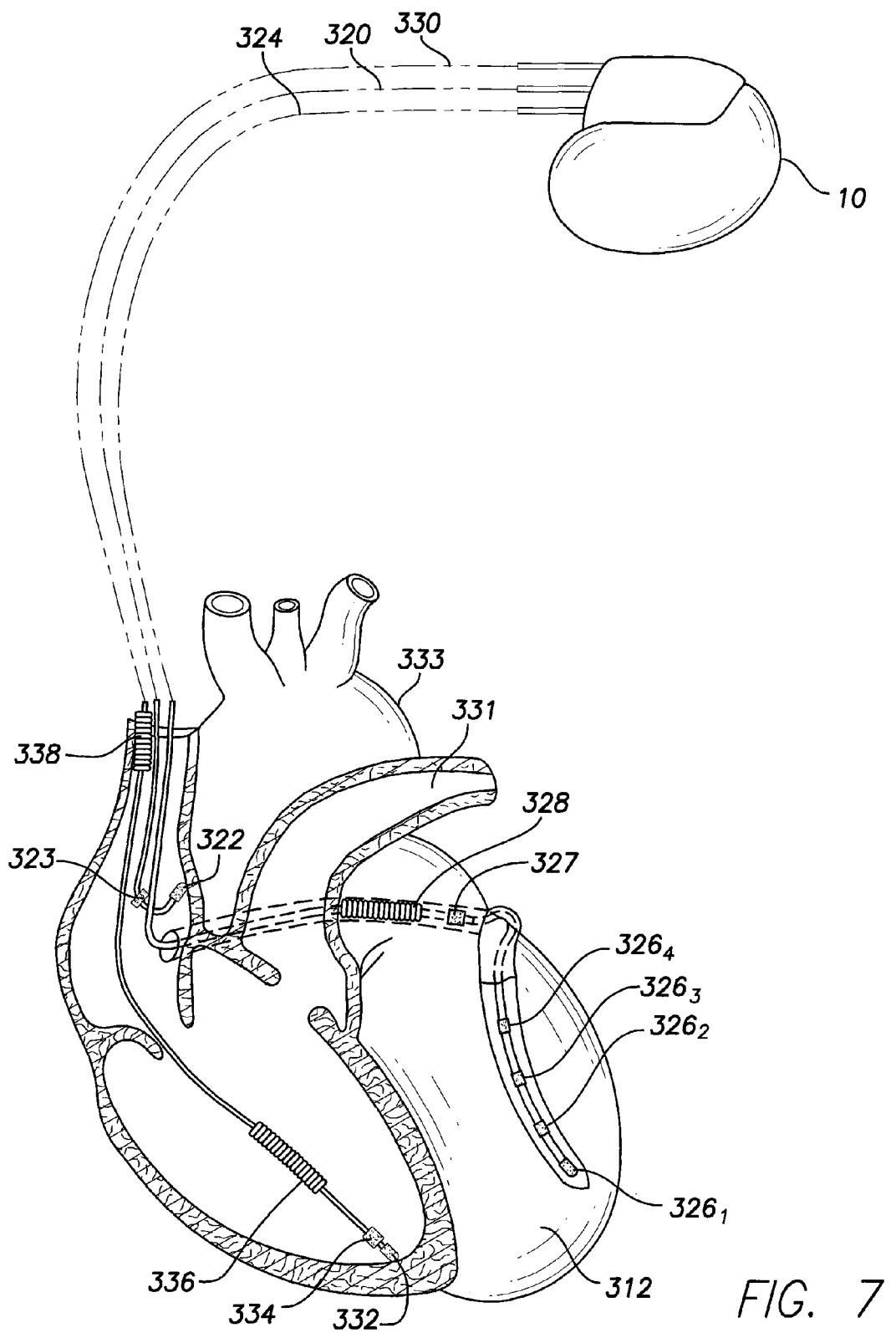
FIG. 7 is a simplified, partly cutaway view, illustrating the pacer/ICD of FIG. 1 along with at set of leads implanted into the heart of the patient.
Figure 8:
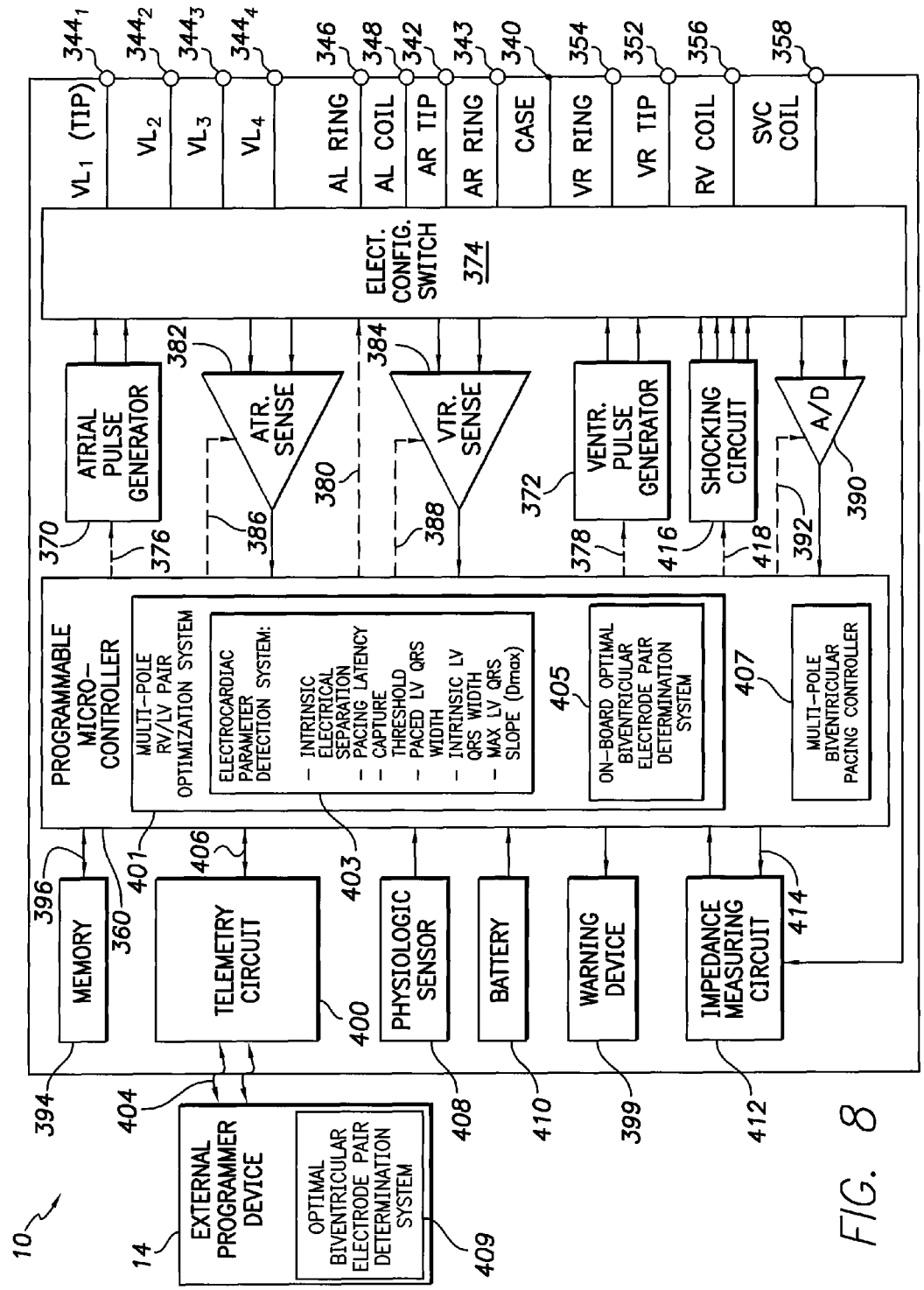
FIG. 8 is a functional block diagram of the pacer/ICD of FIG. 7, illustrating basic circuit elements that provide cardioversion, defibrillation and/or pacing stimulation in the heart and particularly illustrating an on-board electrode pair determination system for determining the optimal RV/LV electrode pair using the techniques of FIGS. 2-6.

With reference to FIGS. 7 and 8, a description of an exemplary pacer/ICD will now be provided. FIG. 7 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a quadra-pole lead), left atrial pacing therapy using at least a left atrial ring electrode 327, and shocking therapy using at least a left atrial coil electrode 328. The $326_1$ LV electrode may also be referred to as a "tip" or "distal" LV electrode. The $326_4$ LV electrode may also be referred to as a "proximal" LV electrode. In other examples, more or fewer LV electrodes are provided. Although only three leads are shown in FIG. 7, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 8, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, $344_1$-$344_4$, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal (VL$_1$ TIP) 344$_1$ and additional LV electrode terminals 344$_2$-344$_4$ for the other LV electrodes of the quadra-pole LV lead.

The connector also includes a left atrial ring terminal (A$_L$ RING) 346 and a left atrial shocking terminal (A$_L$ COIL) 348, which are adapted for connection to the left atrial ring electrode 327 and the left atrial coil electrode 328, respectively. To support right chamber sensing, pacing and shocking, the connector further includes a right ventricular tip terminal (V$_R$ TIP) 352, a right ventricular ring terminal (V$_R$ RING) 354, a right ventricular shocking terminal (V$_R$ COIL) 356, and an SVC shocking terminal (SVC COIL) 358, which are adapted for connection to the right ventricular tip electrode 332, right ventricular ring electrode 334, the V$_R$ coil electrode 336, and the SVC coil electrode 338, respectively. Although not shown in the figure, additional terminals can be provided to accommodate any sub-Q electrodes that might be provided as part of the implantable system.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 8, an atrial pulse generator 370 and a ventricular pulse generator 372 generate pacing stimulation pulses for delivery by the right atrial lead 320, the right ventricular lead 330, and/or the LV lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 382 and ventricular sensing circuits 384 may also be selectively coupled to the right atrial lead 320, LV lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the LV lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 8. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 8, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

An internal warning device 399 may be provided for generating perceptible warning signals to the patient via vibration, voltage or other methods.

Insofar as biventricular pacing is concerned, the microcontroller includes a multi-pole RV/LV electrode pair optimization system 401 operative to perform or control the techniques of FIGS. 2-6, described above, to select a preferred or optimal pair of electrodes for VV pacing. The optimization system includes an electro-cardiac parameter detection system 403 operative to detect one or more of: intrinsic electrical separation between LV and RV; pacing latency in the LV; capture threshold in the LV; paced LV QRS widths; intrinsic LV QRS widths; max LV QRS slopes (Dmax) and/or other relevant parameters. The optimization system 405 also includes on-board optimal biventricular electrode pair determination system that analyzes the detected parameters to determine the optimal RV/LV pair (or some combination of electrodes or electrode pairs for VV pacing.) A multi-pole pacing controller 415 is then operative to control biventricular pacing using the selected electrode pair.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. This is illustrated by way of optimization system 409 shown within the external programmer 14, which is operative to analyze the electrocardiac parameters detected by the device and then transmitted to the external programmer to determine the optimal RV/LV pair (or some combination of electrodes or electrode pairs for VV pacing.) The external programmer then transmits information identifying the selected pair to the pacer/ICD. Note that, when using an external system, a surface ECG can be used to acquire the aforementioned LV QRS width values.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use by an implantable cardiac rhythm management device equipped with a right ventricular lead (RV) with at least one RV electrode and a multi-pole left ventricular (LV) lead having a plurality of LV electrodes, the method comprising:

for each of a selected set of RV/LV electrode pairs, detecting electrocardiac parameters within a patient in which the device is implanted, including parameters representative of an intrinsic biventricular electrical separation between LV and RV and parameters representative of a mechanical contraction delay in the LV; and determining an RV/LV electrode pair for delivering biventricular pacing based on the intrinsic biventricular electrical separation and the mechanical contraction delay.

2. The method of claim 1 wherein detecting parameters representative of intrinsic biventricular electrical separation between LV and RV includes:

for each of the RV/LV electrode pairs, detecting an amount of intrinsic electrical separation ($\Delta_n$) between the RV electrode and the LV electrode ($LV_n$) of the pair.

3. The method of claim 2 wherein determining a RV/LV electrode pair for delivering biventricular pacing includes:

rejecting any RV/LV electrode pairs for the purposes of pacing that lack sufficient intrinsic electrical separation.

4. The method of claim 3 wherein rejecting any RV/LV electrode pairs includes rejecting electrode pairs having less than 30 milliseconds (ms) of intrinsic electrical separation.

5. The method of claim 2 wherein detecting the amount of electrical separation between the RV electrode and the LV electrode ($LV_n$) of the pair includes performing a V sense test to determine the intrinsic electrical separation values for each of the RV electrode/LV electrode pairs.

6. The method of claim 1 wherein detecting parameters representative of a mechanical contraction delay in the LV includes:

for each of the LV electrodes of the selected set of RV/LV electrode pairs, detecting a pacing latency value ($PL_n$) based on pacing pulses delivered using the LV electrode.

7. The method of claim 6 wherein determining a RV/LV electrode pair for delivering biventricular pacing includes:

rejecting any RV/LV electrode pairs for the purposes of biventricular pacing if the pacing latency for the LV electrode of the pair exceeds an acceptable pacing latency value.

8. The method of claim 6 further including detecting a capture threshold for the LV electrode and wherein determining a RV/LV electrode pair for delivering biventricular pacing includes:

rejecting any RV/LV electrode pairs for the purposes of biventricular pacing if the pacing latency for the LV electrode of the pair exceeds an acceptable pacing latency threshold and if the capture threshold also exceeds an acceptable value.

9. The method of claim 6 wherein detecting the pacing latency value includes performing a V pace test for each of the LV electrodes to determine pacing latency values for each of the LV electrode.

10. The method of claim 1 further including determining interventricular ($VV_n$) pacing delays for each of the selected set of RV/LV electrode pairs.

11. The method of claim 10 wherein detecting electrocardiac signal parameters includes:

for each of the RV/LV electrode pairs, delivering biventricular pacing using the interventricular pacing delay ($VV_n$) for the electrode pair and detecting a paced LV depolarization event (paced LV QRS) width for each RV/LV electrode pair.

12. The method of claim 11 wherein detecting the paced QRS event width for each RV/LV electrode pair includes detecting the paced LV QRS event within an electrocardiogram (ECG).

13. The method of claim 1 wherein detecting electrocardiac parameters includes detecting a paced LV depolarization event (paced LV QRS) width for each of the selected set of RV/LV electrode pairs; and wherein determining a RV/LV electrode pair for delivering biventricular pacing includes identifying the RV/LV electrode pair with the shortest paced QRS width and selecting that particular electrode pair for use in delivering biventricular pacing.

14. The method of claim 1 wherein detecting electrocardiac parameters includes detecting a paced LV depolarization event (paced LV QRS) width for each of the selected set of RV/LV electrode pairs;

wherein detecting electrocardiac signal parameters also includes detecting an intrinsic LV depolarization event (intrinsic LV QRS) width for each of the selected set of RV/LV electrode pairs; and wherein determining a RV/LV electrode pair for delivering biventricular pacing includes identifying the particular electrode pair having the shortest paced LV QRS width so long as the paced LV QRS width is less than corresponding intrinsic LV QRS width.

15. The method of claim 1 wherein detecting parameters representative of a mechanical contraction delay in the LV electrocardiac includes detecting a surrogate for a mechanical contraction delay including detecting one or more of pacing latency, pacing delay from LV to RV, and a maximum slope (Dmax) of a paced LV depolarization event (paced LV QRS) for each RV/LV electrode pair; and wherein determining a RV/LV electrode pair for delivering biventricular pacing includes identifying the particular electrode pair having an appropriate mechanical contraction delay and selecting that particular electrode pair for use in delivering biventricular pacing.

16. The method of claim 1 wherein all of the steps are performed by the implantable medical device.

17. The method of claim 1 wherein at least some of the steps are performed by an external device based on signals received from the implantable medical device.

18. A system for use with an implantable cardiac rhythm management device equipped with a right ventricular lead (RV) with at least one RV electrode and a multi-pole left ventricular (LV) lead having a plurality of LV electrodes, the system comprising:

a electrocardiac parameter detection system operative to detect, for each of a selected set of RV/LV electrode pairs, electrocardiac parameters within a patient in which the device is implanted including parameters representative of an intrinsic biventricular electrical separation between LV and RV and parameters representative of a mechanical contraction delay in the LV; and a biventricular electrode pair determination system operative to determine a RV/LV electrode pair for delivering biventricular pacing based on the intrinsic biventricular electrical separation and the mechanical contraction delay.

19. A system for use with an implantable cardiac rhythm management device equipped with a right ventricular lead (RV) with at least one RV electrode and a multi-pole left ventricular (LV) lead having a plurality of LV electrodes, the system comprising:
means for detecting, for each of a selected set of RV/LV electrode pairs, electrocardiac parameters within a patient in which the device is implanted including parameters representative of an intrinsic biventricular electrical separation between LV and RV and parameters representative of a mechanical contraction delay in the LV; and
means for determining a RV/LV electrode pair for delivering biventricular pacing based on the intrinsic biventricular electrical separation and the mechanical contraction delay.

* * * * *